United States Patent
Freeouf

(10) Patent No.: US 6,222,199 B1
(45) Date of Patent: Apr. 24, 2001

(54) ULTRATHIN LAYER MEASUREMENT HAVING A CONTROLLED AMBIENT OF LIGHT PATH

(75) Inventor: John Lawrence Freeouf, Katonah, NY (US)

(73) Assignee: Interface Studies Inc., Katonah, NY (US)

(*) Notice: Subject to any disclaimer, the term of this patent is extended or adjusted under 35 U.S.C. 154(b) by 0 days.

(21) Appl. No.: 09/318,035

(22) Filed: May 25, 1999

(51) Int. Cl.$^7$ .................................... G01N 21/86

(52) U.S. Cl. ............... 250/559.27; 250/225; 356/381
(58) Field of Search ................... 250/559.27, 559.22, 250/559.28, 559.4, 225; 356/381, 376, 364, 369

(56) References Cited

U.S. PATENT DOCUMENTS

| | | | |
|---|---|---|---|
| 3,880,524 | 4/1975 | Dill et al. | 356/118 |
| 4,053,232 | 10/1977 | Dill et al. | 356/118 |
| 4,332,833 | 6/1982 | Aspnes et al. | 427/8 |
| 4,653,924 | 3/1987 | Itonaga et al. | 356/369 |
| 4,672,196 | 6/1987 | Canino | 250/225 |
| 4,762,414 | 8/1988 | Grego | 356/349 |
| 4,837,603 | 6/1989 | Hayashi | 356/369 |
| 5,091,320 | 2/1992 | Aspnes et al. | 43/8 T |
| 5,277,747 | 1/1994 | Aspnes | 156/626 |
| 5,526,117 | 6/1996 | Wielisen et al. | 356/369 |
| 5,595,916 | 1/1997 | Fujimura et al. | 437/8 |
| 5,608,526 | 3/1997 | Piwonka-Corle et al. | 356/369 |
| 5,898,181 * | 4/1999 | Vurens | 250/559.28 |

FOREIGN PATENT DOCUMENTS

| | | |
|---|---|---|
| 63-12906 | 1/1988 | (JP). |
| 6423105 | 1/1989 | (JP). |
| 5-263244 | 10/1993 | (JP). |

OTHER PUBLICATIONS

R.L. Johnson et al, "Spectroscopic Ellipsometry with Synchrotron Radiation", Review of Scientific Inst. vol. 60(7) Jul. 1989 pp. 2209–2212.

Germer et al, "Plarization of Out–of–Plane Scattering from Microrough Silicon", Optics Letters, vol. 22(17) Sep. 1997 pp. 1284–1286.

P.S. Hauge, "Recent Developments in Instrumentation in Ellipsometry", Surface Science, vol. 96, No. 1–3, 1980, pp. 108–140 {Month Unknown}.

Azzam et al, "Analysis of Systematic Errors in Rotating–Analyzer Ellipsometer" Journal of the Optical Society of America, vol. 64, No. 11, Nov. 1974, pp. 1459–1469.

T.E. Faber and R.V. Smith, "Optical Measurements on Liquid Metals Using a New Ellipsometer" Journal of the Optical Society of America, vol. 58, No. 1, Jan. 1968, pp. 102–108.

(List continued on next page.)

Primary Examiner—Que T. Le

(57) ABSTRACT

Metrology for ultrathin dielectric layers of the order of less than 10 nanometers in thickness is achieved by specular ellipsometry in a totally controlled ambient between the light source and the detector, in which, a precise 2.75 through 9.0 eV photon energy range continuum of light is employed. In the signal analysis there is the taking into consideration the effect of noise in the development of the ellipsometric parameter values and in the resulting data. In the invention the precise photon energy range operates to sharpen the identifiability of the change parameters imparted into the reflected light in the ellipsometry while minimizing absorption and signal definiteness masking; and the taking into consideration of noise in the signal analysis involves providing a simulated noise spectrum for comparison with the least squares fitting algorithm-derived parameters to determine the quality of the minimum and the reliability of the inferred parameters.

8 Claims, 3 Drawing Sheets

OTHER PUBLICATIONS

Bertucci et al, "Systematic Errors in Fixed Polarizer, Rotating Polarizer, Sample, Fixed Analyzer, Spectroscopic Ellipsometry", Thin Solid Films 313–314 (1998) 73–78 (Month Unknown).

John L. Freeouf, "Application of Spectroscopic Ellipsometry to Complex Samples", App. Phys. Ltrs. 53,(24), Dec. 1988 pp. 2426–2428.

D.E. Aspnes, Analysis of Semiconductor Materials and Structures by Spectroellipsometer, SPIE vol. 946, 1988 pp. 84–97 (Month Unknown).

Kenneth K. Ellis, "Polarimetric Bidirectional Reflectance Distribution Function of Glossy Coatings", J. Opt. Soc. Am., vol. 13, No. 8, Aug. 1996 pp. 1758–1762.

Deumié et al, "Ellipsometry of Light Scattering from Multilayer Coatings", Applied Optics, vol. 35 No. 28, Oct. 1996, pp. 5600–5608.

U. Rossow et al, "Interpretation of Surface–Induced Optical Anisotropy of Clean, Hydrogenated, and Oxidized Vional Silicon Surfaces Investigated by Reflectance Difference Spectroscopy", J. Vac. Sci. Tech, B, 14,4, Jul./Aug. 1996 pp. 3070–3074.

* cited by examiner

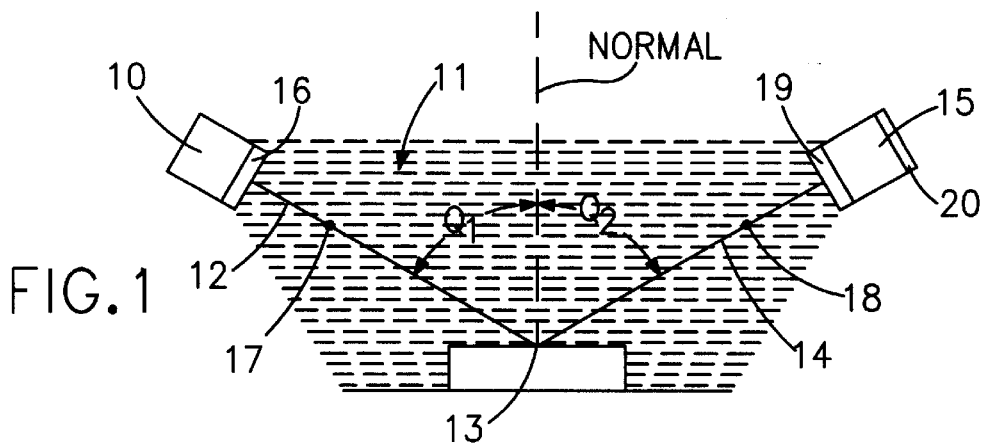

FIG. 1

IN A SPECTRAL MONOCHROMATIC BIDIRECTIONAL ELLIPSOMETRY APPARATUS PROVIDE A 2.75–9.0 eV PHOTON RANGE CONTINUUM LIGHT SOURCE IN A CONTROLLED ENVIRONMENT BETWEEN LIGHT SOURCE AND LIGHT DETECTOR — 30

PROVIDE ALL MECHANICAL AND ELECTRICAL ADJUSTMENTS AND CALIBRATIONS TO SET THE ANGLE OF INCIDENCE AND TO FULLY REFER THE POSITIONS OF POLARIZING COMPONENTS AND THE PHASES OF ELECTRICAL SIGNALS TO THE PLANE OF INCIDENCE — 31

PERFORM ANALYTICAL OPERATIONS IN REFINING AN INITIAL ASSUMPTION OF SAMPLE PARAMETERS SUCH AS COMPOSITION AND THICKNESS BY TAKING CLOSELY SPACED DATA POINTS OVER THE ENTIRE WAVELENGTH RANGE, COMPARING PREVIOUSLY TABULATED RESULTS BASED ON SIMILAR SAMPLE PARAMETERS WITH THE DATA BEING TAKEN, AND ITERATIVELY MODIFYING THE PARAMETERS TO MINIMIZE ANY DISSAGREMENT BETWEEN THE DATA ON THE ASSUMPTION AND THE DATA BEING TAKEN, USING SIMULATIONS WITH ADDED NOISE TO DETERMINE THE ATTAINABLE QUALITY OF THE INFERRED PARAMETERS — 32

FIG. 2

ULTRATHIN LAYER MEASUREMENT HAVING A CONTROLLED AMBIENT OF LIGHT PATH

CROSS REFERENCE TO COPENDING APPLICATION

Cross Reference is made to application Ser. No. 09/160,017, Filed Sep. 24, 1998, of John L. Freeouf, titled HIGH PHOTON ENERGY RANGE REFLECTED LIGHT CHARACTERIZATION OF SOLIDS, assigned to the assignee of this application, and incorporated herein by reference.

FIELD OF THE INVENTION

The invention relates to highly sensitive metrology involving ellipsometry in the accurate measurement of layers, such as the gate dielectric of a semiconductor device, that are of the order of less than 10 Angstroms in thickness and in particular to the achievement of accuracy in that thickness range.

BACKGROUND OF THE INVENTION AND RELATION TO THE PRIOR ART

Major efforts in the art are currently being directed to a form of ellipsometry in which the light is incident to and reflected from a sample under study at angles with respect to that sample. Changes in polarization of a reference polarized light resulting from variations of the angles, and changes in light both in and out of the plane of incidence are the measured quantities. In ellipsometry, one determines the amplitude and polarization of the reflected beam as a function of the polarization, wavelength and angle of incidence of the incident beam, as well as of the deviation of the measured direction. This deviation being defined in the two directions of "within" and "perpendicular to", the plane of incidence.

While the principles are useful in many types of characterization measurements, each situation in which the principles are applied will involve a number of considerations that are unique to that situation.

In order to establish a perspective in the application of the technology; the semiconductor industry is used as an illustration for the reasons that the technology is quite amenable to such considerations as the dimensions being small, that the characterization of the material under study usually be non-destructive and that there be an ability to make monitoring determinations in real time. In the semiconductor industry the principles of ellipsometry have been extensively applied to the types of material characterizations needed to meet the ever decreasing dimensions encountered in devices and in their fabrication.

The present technology has been yielding satisfactory results where the dimensions under study are above ten of nanometers(nm) but it is becoming increasingly difficult to get the accuracy needed. Current expectations in the semiconductor device technologies are toward electrode dimensions such as gate widths of the order of 0.25 micrometers in the year 1998, progressively becoming narrower to about 0.1 micrometers by the year 2007. Dielectric thicknesses must shrink to meet the electrode dimensions for a gain in performance to be realized. The dielectric thickness must therefore shrink from about 4.0 nanometers(nm) in the year 1998 to about 1.5 nm in the year 2007. Further such dimensions will probably be made up of several thinner layers. Metrology is a necessary corrollary to achieving these technologies. It is necessary to be able to measure a dimension in order to be able to properly control it. The thicknesses and tolerances predicted to be necessary in the coming technology cannot be properly measured and characterized with current technologies.

SUMMARY OF THE INVENTION

Improvements in accuracy and sensitivity of metrology for material dimensions of the order of less than 10 nanometers are achieved through the providing of specular ellipsometric characterization such as BiDirectional Ellipsometry(BDE) in a totally controlled ambient between the light source and the detector, in which, a precise 2.75 through 9.0 eV photon energy range continuum of light is employed. The specular ellipsometric precise energy range light is interdependently particularly effective together with, in the signal analysis, of the taking into consideration the effect of noise in the development of the ellipsometric parameter values and in the resulting data. In the invention the precise photon energy range operates to sharpen the identifiability of the change parameters imparted into the reflected light in the ellipsometry while minimizing absorption and signal definiteness masking; and the taking into consideration of noise in the signal analysis involves providing a simulated noise spectrum of comparison with the least squares fitting algorithm-derived parameters of the sample to help determine the quality of the minimum and the reliability of the inferred parameters of the sample.

BRIEF DESCRIPTION OF THE DRAWINGS

FIG. 1 is a schematic illustration of the features involved in a spectral ellipsometric metrology system with a controlled ambient.

FIG. 2 is a flow diagram of the structural and analytical aspects involved in the ultra thin layer measurement of the invention.

FIGS. 3 to 5 are graphs of signals in the precise photon energy range continuum of light of the invention illustrating the variation of the highly useful ellipsometric parameters; wherein:

FIG. 3 is a graph of Photon energy (eV) vs Tan Psi (ψ) illustrating the divergence of the signal that occurs in the highest, beyond about 6 eV photon energy range.

FIG. 4 is a graph of Photon energy (eV) vs Cos Delta (Δ) illustrating a divergence of the signal that occurs in the higher, beyond about 5 eV photon energy range.

FIG. 5 is a graph of Photon energy (eV) vs the derivatives of real and imaginary bulk dielectric constants indicating that different paths are followed in the above 6 eV photon energy range.

DESCRIPTION OF THE INVENTION

Figure 3:
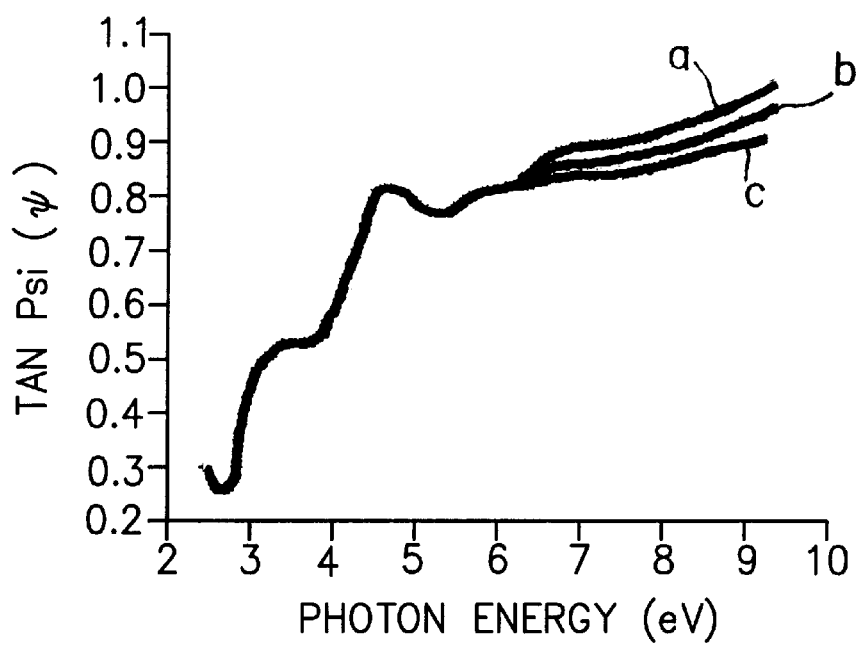

In the sub 10 nm dimensional range, control must be exercised with respect to factors in both the ellipsometry apparatus structure and in the analytic effort. In the invention; the photon energy of the light is in a relatively precise range that is high enough to achieve the tradeoffs involved in acquiring the information needed but not so high that the photons will damage the materials in the system, that the range be such that relatively standard light sources used in the art can be used, and that the controlled ambient provided between the light source and the detector be such that absorption and masking of signal definitiveness is prevented. In addition, in the analytic operations the presence of noise, which is always present, is taken into consideration by applying the same least squares fitting algorithms to both the data taken from the sample under study and to simulations of similar spectra to which known amounts of noise are added to help establish the "goodness of fit" of the data and the quality of the parameters of the sample inferred by comparison to the simulations of various noise levels with previously tabulated known quality of parameters.

The apparatus of FIG. 1 is preferably a specular BiDirectional Ellipsometry (BDE) apparatus in which light from a source passes through a reflection from the sample under study to a detector in which the incident and the reflected light paths are in a single plane with equal angles of incidence and reflection; and where a difference in polarization between the incident and the reflected light beams contains the characterization desired. It has been found that the specular BDE instrument has fewer places where error introducing misadjustment can occur, and that the equations used in understanding the data produced, are simpler.

Referring to FIG. 1, a schematic illustration of the principles of the invention is provided. In FIG. 1 the relatively precise about 2.75 through about 9.0 eV photon energy range monochromatic light source 10 provides a continuum of light through a range that includes the photon energies wherein information containing branches of the signal curves occur as will be described in connection with FIGS. 3–5. The light source 10 or the detector 15 may have monochromatic capability such as adjustability so that the light can be separated into individual wavelength regions thereby enhancing the ability to increase data points. In the precision needed for measurement in the sub 10 Angstrom thickness range insufficient energy anywhere in the range will fail to produce the signal information needed and too must energy can damage the material under study. Examples of preferred light sources currently available in the art that have the desired photon energy range of about 2.75 through about 9.0 eV, are deuterium and hydrogen lamps. A reason for the preference is that the light beam is uninterrupted or is a continuum up through the desired range with these sources.

A controlled ambient 11 throughout the entire light path 12 from the source, through the reflection from the sample at 13 and the reflected light path 14 to the detector 15, is provided, the function of which is to prevent such interactions as absorption and local exitation from reducing the distinguishability of the signal delivered to the detector 15. The controlled special ambient 11 may be a normal vacuum (<0.01 torr) or an inert gas such as helium or nitrogen, that would be non-absorbing under the conditions involved.

A window member 16 is provided for the light source 10 that performs at least the functions of: not deteriorating or absorbing in passing the desired photon energy range of light; of passing only the desired photon energy range light while preventing any contamination from the light source from entering the ambient; and preventing the ambient from coming into contact with the light source. As examples, some light sources may involve an arc and others may involve the element deuterium, both have downside aspects that are undesirable if they get into the ambient. The arc may include unwanted gasses and the deuterium may burn in the atmosphere. The window element 16 should confine any unwanted aspects of the light and any gas generated. It is shown as a single element although it will be apparent that an many individual members as are needed to perform the necessary overall function may be used. While there are many types of windowing component elements available for use in achieving different purposes, the ingredients of any component that is employed must always be able to pass the desired photon range light at the point in the light path where employed without introducing unacceptable attenuation of the light or having the ingredient deteriorate. Windows can be placed at many positions in the optical path, thereby permitting the separation of different ambients and improving component accessibility.

Known polarization would be introduced in the incident light path 12 at a location such as 17, and the polarization of the reflected light path 14 would be in essence measured at a location such as 18. The polarization components may be passive such as multiple brewster angle reflections. There is an advantage for sensitivity that the light passing through the combined polarizer elements be extinguished so that any light that passes be the result of polarization changes produced by the sample under study. The polarization may also be of the rotating element type in which a waveform that is associated with the time dependence of the signal that is caused by the rotating element. A Fourier analysis produces clearly distinguishable terms. In a rotating polarizer—sample— fixed polarization analysis system there will be clearly distinguishable ( ) and ( ) related term. While there are many types of polarization components available for use in achieving different purposes, the ingredients and the optical properties must always be able to achieve the intended purpose without attenuation or deterioration. Where moving parts are involved outgassing of lubricants is a consideration. The material $MgF_2$ has been used in the art for polarizers.

The materials $MgF_2$ and LiF are suitable for windows and filters. The detector 15 must be responsive to the distinguishing features of the output signal in the reflected light path 14. There a number of types of detectors in the art varying in cost, area covered and sensitivity. The usual detectors in the art employ circuitry selected from photomultiplication, charge coupled device arrays and diode arrays.

The detector element 15 is equipped with a windowing and filtering element 19 that performs the functions of keeping anything from the ambient side out of the detection operation and anything from the detection operation side out of the ambient. While there are many types of windowing and filtering elements that can be used in achieving different purposes, the elements that are employed must always be able to pass the relatively precise about 2.75 to 9.0 eV photon range of light in the light path without introducing unacceptable attenuation of the light or having the material deteriorate with the passing the incident light. The materials LiF and $MgF_2$ are also satisfactory for those windows and filters.

In the practice of the invention where the desired measurements are as fine as is the case with ultra thin layers in the sub 10 Angstrom (Å) range, in accordance with the invention, the signal from the detector element 15 is processed using standard ellipsometry equations. Simulations to which a known amount of noise has been added are subjected to the same analysis, and comparison between these results and their RMS error or "goodness of fit", facilities judgements to be made concerning the quality of the inferred ellipsometric parameters and the likelihood of being close to a global minimum. The analysis is depicted as occurring in element 20.

In FIG. 2 a flow chart is provided illustrating the general procedure that is employed in achieving the ultra thin layer measurement of the invention.

Referring to FIG. 2, in a first step 30, in a spectral monochromatic BDE ellipsometry system such as shown in FIG. 1, in which incidence and reflection angles, $0_1$, and $0_2$, of the light beams 12 and 14 respectively, from the sample under study are equal, that is $0_1$ and $0_2$ are equal, and the 2.75 through 9.0 eV range of light is provided. The light being monochromatic permits separation into individual wavelength regions which in turn enhances the ability to increase the points at which data is taken. The ambient between the light source and the detector is controlled, such as by being in a vacuum, so as to prevent absorption and local excitation. Polarization is applied to the incident light beam 12 at 17 and the effect on that polarization in the reflected beam 14 introduced from the reflection from the sample at 13 is evaluated at 18. In general the effect on the polarization at 18 is in terms of the standard ellipsometric parameters Tan Psi ($\psi$) and Cos Delta ($\Delta$). The variation of values is observed over a number of data points taken at different photon energies.

The specific range and condition of the light source is provided to perform the function of the light source 10 of FIG. 1 delivers a continuum of sufficient light for the metrology in a photon energy range of from a minimum of about 2.75 eV through about 9.0 eV. In the precision needed for measurement in the sub 10 Angstrom thickness range, insufficient intensity anywhere in the range will fail to produce the signal information needed, and too much intensity and/or too high a photon energy can damage the materials under study.

In step 31 the ellipsometry system is adjusted is adjusted mechanically, optically and electrically to confine any polarization change appearing at 18 to that produced by reflection at 13 from the sample under study. In the system angle $0_1$ must equal angle $0_2$ the incident and the reflected light beams 12 and 14 must be in the same plane. In adjustment, having a sample holding fixture that permits rotation in the plane of the reflecting surface of the sample, is helpful. There are many components available in the art such as monochromators and autocollimators for light, and goniometer sample mounting elements.

In step 32 the iterative analytical operations take place. In general the analysis begins with a model or with an initial assumption of the composition and thickness of the sample under study. Data is then taken over the entire wavelength range. Least squares fitting algorithms with the consideration for noise of the invention, are employed in minima analysis in search of a principal or global minimum. In accordance with invention the fitting algorithms provide a "goodness of fit" type of measurement between model calculation and the data that is taken and is compared with that found in tabulations using noise containing simulations. Where the calculated data and the taken data are similar and the statistical error bars used in the art are also similar then the reliability of any parameters inferred from the data comparison is likely to be similar. The high quality parameter values produced are then correlatable with the types of information essential in the characterization, or identification of quality features of the composition, of the surface and of the bulk of a sample of material under study.

In the following FIGS. 3–6 the graph scales and the discussion are directed as perspective examples of the analysis of a small dimension sample of a material, of the order of 5 nanometers or less, such as would be encountered in the characterization of the gate insulator of a semiconductor field effect transistor.

Referring to FIG. 3 there is shown a graph of the standard ellipsometry signal Tan Psi ($\psi$), which is the ratio of the two polarization dependent reflection coefficients and one of the variables measured by ellipsometry, as a function of the photon energy (eV). The graph shows the type of correlation available with the 2.75–9.0 eV photon energy range of the invention in which illustrative properties of particular layers in a sample of a material are distinguished.

In the graph of FIG. 3 there is a single signal in the eV range below about 6 eV, which is about the upper limit of conventional ellipsometry. In that range signal, the differences produced by sub 10 nm features are too small for resolution in the signal, whereas, within the range about 6 eV the features become apparent and the signal diverges into three separate traces a,b and c, each of which is identifiable with a property of the sample. As an illustration, consider the data to be describing a three layer oxide/nitride/oxide structure on a substrate with a total thickness of about 4.0 nm such as used in the semiconductor art to prevent dopant depletion, reduce interface roughness and improve pinhole hardness, with the 4 nm thickness of the sample under study divided between the three layers. Although five separate structures are involved only the three types of curves a, b and c are seen because the controlling variable is the total thickness. There is a first layer of silicon dioxide ($SiO_2$) on the substrate, there is a center layer of silicon nitride($Si_3 N_4$) and there is a surface layer of silicon dioxide ($SiO_2$). Since the total dielectric thickness is fixed at 4.0 nanometers in each of the samples under study the layer thickness variations will then only be in the individual layers of $SiO_2$ and the $Si_3 N_4$ center layer.

In the range about 6 eV photon energy, in the diverged three, separate, readily distinguishable curves labelled a, b, and c, that correspond to the specific samples. The sample for curve a is a structure of a 2.0 nm layer of $SiO_2$ on a 0.5 nm layer of $Si_3 N_4$ that in turn is on a 1.5 nm layer of $SiO_2$. The sample for curve b is a structure of a 2.0 nm layer of $SiO_2$ on a 1.0 nm layer of $Si_3N_4$ that in turn is on a 1.0 nm layer of $SiO_2$. The sample for curve c is a structure of a 2.0 nm layer of $SiO_2$ on a 1.5 nm layer of $Si_3N_5$ that in turn is on a 0.5 nm layer of $SiO_2$. The divergences of the branches a, b and c at 9 eV photon energy light is such that a difference in thickness range of the $SiO_2$ layer next to the substrate varied from 0.5 to 1.5 nm; while the top layer remained constant at 2.0 nm; produced a readily identifiable, almost 0.3 difference in value of Tan Psi ($\psi$).

The 2.75–9.0 eV range of the invention is influenced by the facts that in the curve of FIG. 3 there is an abrupt change of direction below the 2.75 portion of the range and at the upper portion of the range, while the a, b, and c,signals continue to diverge above 9.0 eV, they are sufficiently detectable at 9.0 eV so that the greater noise levels and potential for increase in material damage at higher photon energy is avoided.

Figure 4:
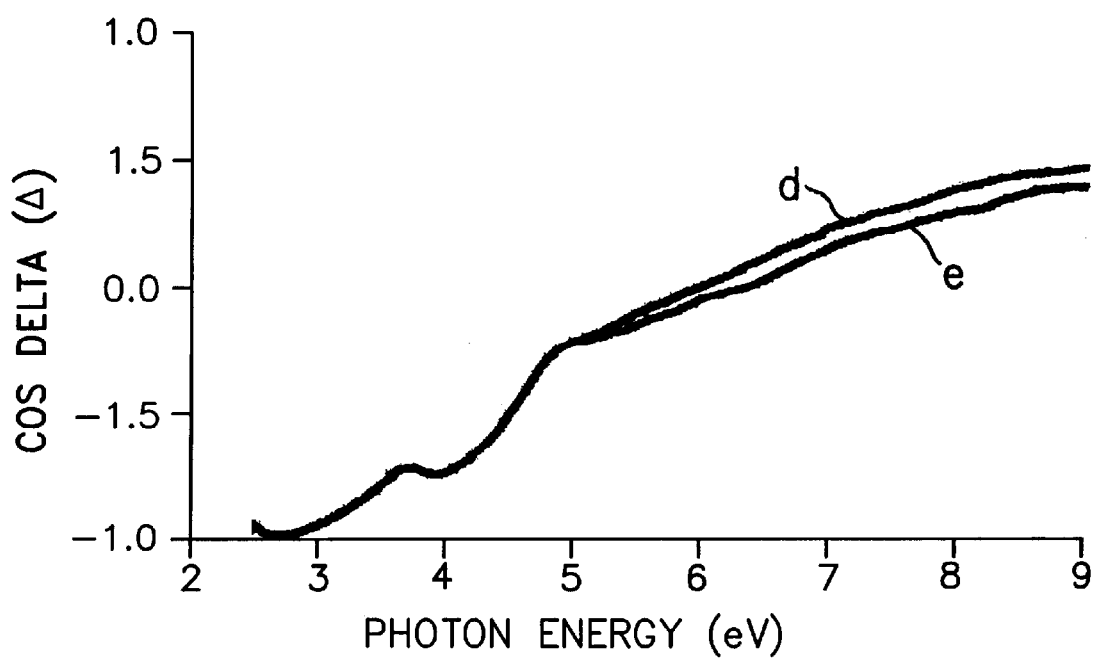

Referring to FIG. 4 is a graph is shown further illustrating the increased analysis sensitivity achieved with the precise photon range ellipsometry of the invention. In FIG. 4 the graph is of Photon energy (eV) vs the standard ellipsometry output signal Cosine Delta ($\Delta$), and illustrates the use of the invention in the metrology of changing the thickness of the nitride layer in a sample of oxide/nitride/oxide on a substrate while maintaining the constant 4 nm total thickness. The graph indicates an abrupt reversal near 2.75 eV followed by a single continuum in the range up to about 5 eV and thereafter in the continuum a divergence into separate branches labelled, d and e, in the photon range approaching 9 eV. The divergence of the signal into the d and e branches is sensitive to the thickness dimension of an individual layer of the sample of material.

Considering the sample of material under study in FIG. 4 to be of three layers on a silicon substrate. If there is a 2.0 nm surface layer of SiO$_2$ on a 1.5 nm layer of Si$_3$N$_4$ that in turn is on a 1.0 nm layer of SiO$_2$ on a substrate such as Si; then the curve of branch d would be produced. When the thickness of the center, Si$_3$N$_4$ layer is reduced from 1.5 nm to 1.0 nm, the curve follows the branch e. The difference between the branches d and e at the higher photon energy range result in a difference of about 0.02 in the Cosine Delta ($\Delta$) value for use in characterization analysis. The gains follow in part from reduced wavelength of the higher energy photons and they are also due in part to the fact that optical prpoerties of constituents all change substantially in the higher photon energy range. For example SiO$_2$ and Si$_3$N$_4$ both become highly absorbing whereas the dielectric functions of Si are smaller in the higher photon energy ranges than for the lower photon range of up to 6 eV used heretofore in the art. This provides a larger range of variation of parameter space with which to perform analysis.

Figure 5:
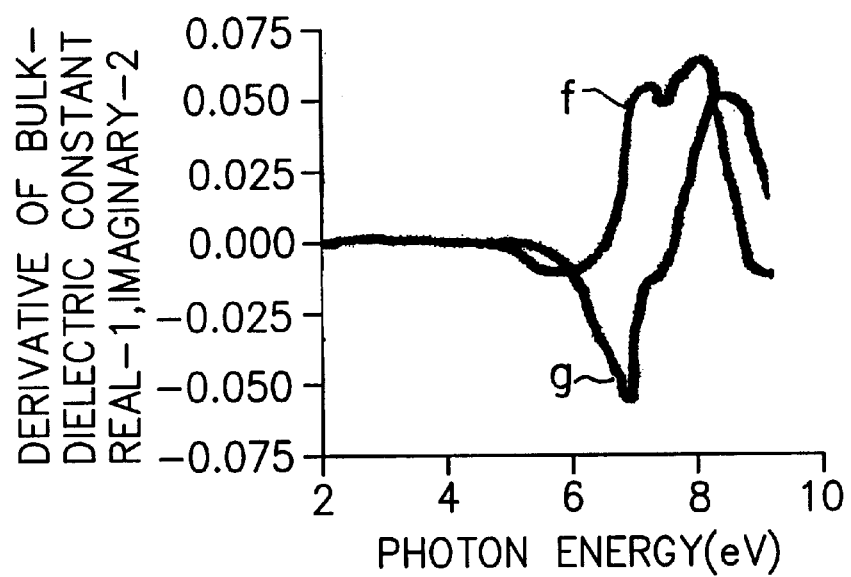

Referring to FIG. 5 a graph is provided of the values of the real and the imaginary derivatives of the bulk dielectric constant vs the photon energy (eV) of an example material (SiC) illustrating the act that in the extended photon range of the invention the curves representing the values of the real, f, and the imaginary, g, derivatives take independent and completely distinguishable paths. The branches f and g begins to diverge about 4 eV and take completely different paths in the higher eV ranges. For many material surfaces the derivative of the bulk dielectric constant is a measure of the surface condition and the magnitude of the signal represented by the curve can be scaled to a measure of step density. The divergent paths of FIG. 5 permit, in an analysis, the distinction of surface and interface roughness, island formation and steps, and are of particular value where the material under study has a high band gap such as silicon carbide (SiC) and Gallium Nitride (GaN). Signals of the type in FIG. 5 may be used in predictions of the applications of the techniques of the invention to SiC.

Figure 6:
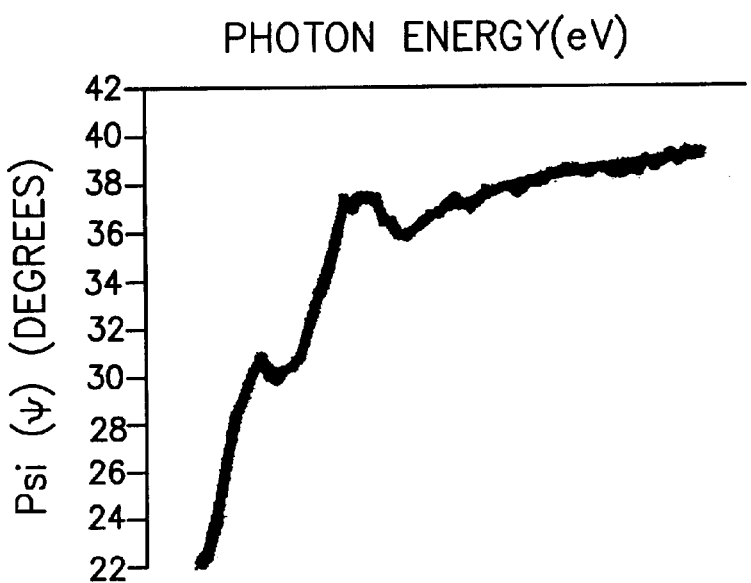
FIG. 6 is a schematic graphic illustration of the superpositioning of a noise component onto a simulation of Psi (ψ) ellipsometric parameter with photon energy.

Referring to FIG. 6, as the data is analyzed, the Psi($\psi$) ellipsometric parameter with respect to Photon Energy(eV) follows a curve similar to the Psi ($\psi$) example in FIG. 6, and the superimposed noise varies the value slightly at each point. Similarly the noise is superimposed on the Delta ($\Delta$) ellipsometric parameter.

The following example equations 1 and 2 are employed in the analysis.

The equations are the types standard in the art such as those reported by T. E. Faber and N. V. Smith in the Journal of the Optical Society of America, 58, 102, (1968).

$$\epsilon_1 = \sin^2\varphi\tan^2\varphi\frac{(\cos^2 2\psi - \sin^2\psi\sin^2\Delta)}{(1+\cos\Delta\sin 2\psi)^2} + \sin^2\varphi \qquad \text{Eq. 1}$$

$$\epsilon_2 = 2\sin^2\varphi\tan^2\varphi\frac{\sin 2\psi\cos 2\psi\sin\Delta}{(1+\cos\Delta\sin 2\psi)^2}. \qquad \text{Eq. 2}$$

Where E$_1$ and E$_2$ are real and imaginary dielectric functions at that photon energy and the angle of incidence is 0 or $\psi$.

Where the conditions of the equations are not precisely met, various models and approximations may be used to obtain an estimate of the true function.

In the analysis of the signal in the optical path 14, in the use of ellipsometric analysis to determine such parameters as thickness, the use of least squares fitting algorithms in a computing environment are employed. In such algorithms there are possibilities of multiple minima which in turn results in having to deal with whether a particular minimum is "local" or whether it is the sought "Global" minimum. In accordance with the invention the "goodness of fit" between model calculation and the actual data taken is compared with tabulations using noise simulations; from the quantities from this comparison there is derived a measure of the noise level of the data as well as the quality of the model fit, which thereby helps to identify whether other local minima having similar "goodness of fit" values will exhibit parameters within acceptable error bars from those of the present fit. If each major iteration with the noise enhanced fit of the invention always goes to the same parameters an assumption can be made that the situation is close to a "Global" minimum. In an "on going" product testing mode there may not be time for minimum seeking iterations so that a wide range of initial assumptions based on experience with similar product may frequently yield the desired "Global" minimum.

In a situation where different parameters are encountered with different initial assumptions then local minima are being encountered. In a case such as this, the difference between the current test results and the modeling curves, is employed. The root mean square (RMS) value of this difference is generally called "goodness of fit" or some similar term. The amount of difference in the term for different "local" minima is a useful criterion for use in deciding whether the different sets of parameters can really be distinguished by the test data. If the difference is small then the different sets are not being reliably separated. A minimum may be considered to be shallow where the data is insensitive to the parameters being varied. One way the depth of a minimum can be measured is with respect to the noise level of the data.

Two types of semiconductor device ultra thin layer gate dielectric structures that are expected to be of critical importance in semiconductor device technology in the coming decade. A first is oxide/nitride/oxide "ONO" which is a layer of SiO$_2$ on a layer of Si$_3$N$_4$ on a layer of SiO$_2$ on a silicon substrate and the second is oxide/nitride "ON" which is a layer of SiO$_2$ on a layer of Si$_3$N$_4$ on a silicon substrate. The interfaces between these layers may be gradual rather than abrupt depending on the technology by which they are made.

The combined features of the invention of the use of the selected precise photon energy range in a controlled environment together with with the taking into consideration of the noise that would be present in a real situation in the RMS fitting in analysis provide the benefits that permit accurate metrology of type of ultra thin layers that will be needed in the future.

A benefit illustration is provided in connection with the following Table 1 for an oxide-nitride-oxide type ultra thin layer structure and in Table 2 for an oxide-nitride type ultra thin layer structure; for three levels of simulated noise Low (0.05), Med (0.2) and High (0.5). In the tables, the columns labelled a illustrate the inferred total thickness using conventional ellipsometer equipment where photon range is 1.5–5.5 eV, and in the section labelled b where the precise range of 2.75–9.0 eV is employed in the ellipsometer of FIG. 1. The tables indicate much greater thickness sensitivity and the ability to reliably measure sub 10 nanometer thicknesses in the types of structures essential for future needs.

TABLE 1

| Structure (O, N, O) | a | | | | | | b | | | | | |
|---|---|---|---|---|---|---|---|---|---|---|---|---|
| | Noise: | | | | | | | | | | | |
| | Low (0.05) | | Med (0.2) | | High (0.5) | | Low (0.05) | | Med (0.2) | | High (0.5) | |
| | $\Delta_N$ % | $\Delta_O$ % | $\Delta_N$ % | $\Delta_O$ % | $\Delta_N$ % | $\Delta_O$ % | $\Delta_N$ % | $\Delta_O$ % | $\Delta_N$ % | $\Delta_O$ % | $\Delta_N$ % | $\Delta_O$ % |
| 6Å, 4Å, 6Å | 3 | 2 | 33 | 19 | | | .4 | .6 | 4 | 6 | | |
| 7Å, 4Å, 6Å | 6 | 3 | 21 | 11 | | | | | 3 | 3 | | |
| 7Å, 5Å, 5Å | 1 | .5 | 20 | 14 | | | .4 | .7 | 1 | 3 | 6 | 8 |
| 7Å, 4Å, 5Å | | | | | | | .8 | .8 | | | 6 | 7 |

TABLE 2

| Structure (O, N) | a | | | | | | b | | | | | |
|---|---|---|---|---|---|---|---|---|---|---|---|---|
| | Noise: | | | | | | | | | | | |
| | Low (0.05) | | Med (0.2) | | High (0.5) | | Low (0.05) | | Med (0.2) | | High (0.5) | |
| | $\Delta_O$ % | $\Delta_N$ % | $\Delta_O$ % | $\Delta_N$ % | $\Delta_O$ % | $\Delta_N$ % | $\Delta_O$ % | $\Delta_N$ % | $\Delta_O$ % | $\Delta_N$ % | $\Delta_O$ % | $\Delta_N$ % |
| 3Å, 8Å | 19 | 9 | 47 | 12 | 100 | 24 | 5 | .1 | 19 | 3 | 44 | 7 |
| 3Å, 9Å | 32 | 29 | 19 | 4 | 13 | 7 | .1 | .3 | 5 | 2 | 22 | 5 |
| 4Å, 7Å | 3 | .1 | 10 | 4 | 150 | 54 | .7 | .4 | 3 | 2 | 9 | 5 |
| 4Å, 8Å | 0 | .4 | 6 | 4 | 20 | 5 | 1+ | .6 | 5 | 3 | 14 | 6 |
| 5Å, 7Å | 27 | 11 | 56 | 45 | 30 | 11 | .8 | .6 | 3 | 2 | 16 | 8 |
| 5Å, 8Å | 14 | 5 | 12 | 3 | 28 | 13 | | | | | | |
| 6Å, 6Å | 42 | 25 | 33 | 23 | 100 | 77 | .5 | .7 | 1+ | 2+ | 19 | 11 |
| 6Å, 7Å | 43 | 21 | 15 | 6 | 25 | 14 | 1 | .9 | 3 | 2+ | 14 | 8 |
| 6Å, 8Å | 12 | 4 | 25 | 13 | 13 | 5 | 1 | .6 | 3 | 3 | 16 | 8 |

The large scatter of values and errors found in the columns under the heading "a" are indicative of shallow local minima not closely related to the global minimum. The rather consistent and small errors in the columns under the heading "b" are indicative of local minima that are closely related to the rather deep global minimum, and hence in accordance with the invention, provide reliable sample parameters.

Some perspective involving the terminology concerning the apparatus, the sensitivity achieved and the use of the data would appear to advance the explanation of the invention.

It will be apparent that the terminology in the invention specifying a controlled ambient is relative and involves pragmatism in the following way. The effect of the ambient on the characterization ability involves both the length of the optical path as well as with any interaction affecting the information in the light along the way and the required sensitivity to get the desired information.

In accordance with the invention the entire optical path from the light source to the detector is to be held within the control limits, including the distance inside the light bulb from the point light source to the incident light path. Taking as an example a wavelength situation wherein a two meter optical path in a normal atmosphere would lead to a 99% absorption. While 99% would normally be unacceptable, if the optical path in an absorbing environment could be reduced to two centimeters, there would then be an about 99% transmission of the light in the optical path and the possibility that sufficient information could be acquired. A theoretical ideal would be where the optical path were sufficiently shortened or where the environment in whatever optical path is used is rendered non or minimally absorbing such as by blowing into the optical path a non absorbing gas to keep the absorption from an information extraction standpoint, to within a tolerable range. There are structural options such as building the system so that the sample is mostly out of the absorbing optical path that can help but they usually lead to difficult tradeoffs elsewhere in the apparatus and information processing, design. Generally, enclosing the entire light path within an evacuated housing is a very efficient construction.

Additional benefits from the use of the 6 eV–9 eV higher energy photon part of the precise range of the invention are that they of necessity have the shorter wavelengths (The wavelength λ is proportional 1/the photon energy E). Since optical determination of thickness of the sample under study may involve interference fringes, which occur with a spacing of the order of nd/wavelength(λ), where n is the index of refraction and d is the physical thickness because as the wavelength becomes smaller the fringe spacing will increase where all else remains fixed. A limitation exists in that absorption often increases as energy does so that smaller thicknesses may be required to be able to see the fringes. Since light scattering terms in the ellipsometrical parameters ψ and Δ scale as the ratio of the particle size to the wavelength, a smaller wavelength will permit observation of smaller particles.

In the illustration under discussion, that of the semiconductor industry, in the processing there are situations where it is necessary to determine the thickness and composition of several layers. To make such determinations routinely it is necessary to establish the value of the dilectric constant of the materials under study. A model is then set up of the sample structure in which the layers and interfaces to be involved in the characterization to be performed are built into the initial assumption and typically approximated by a version of the effective medium approximation either of the bulk end point constituents or intermediate separate measured compositions.

From the sensitivity and accuracy that becomes available through the invention, within the background of the modeling, sufficient accuracy is achieved that calculations can establish the optical response that the sample of the material under study will provide, in comparison to experimentally determined results. With computerized iteration and parameter modification, discrepancies are thus reduced between the model and the experimental results. When agreement is sufficiently close, as defined as being within the statistically determined error bounds in the necessary parameter, there will then have been achieved, a measurement of the parameters involved.

The technique being described here and as in previous discussion, the invention is applied in connection with the standard least squares fitting technique used in the art. In all least squares type fitting, care and cross checking, is always advisable to make sure that the model remains correct, that the initial parametric assumptions remain valid and that the proper local minimum for the errors is being used.

There are occasions in characterization operations where it is advantageous to simply determine the dielectric spectrum of a material. Where the sample of the material is opaque, sufficiently thick and atomically smooth, the ellipsometric parameters may be inverted to directly provide the dielectric function of the material employing the equations 1 and 2 previously discussed.

What has been described is a technique of reflected light characterization of ultra thin layers of solid materials that makes possible accurate measurement in the sub 10 angstrom thickness region involving a specular ellipsometric apparatus using a precise 2.75 to 9.0 eV photon energy range continuum light in a controlled ambient and taking into consideration the effect of a noise increment in the least squares fitting identification of the global minimum and the ellipsometric parameters.

What is claimed is:

1. In metrology apparatus for the measurement of characteristics of a solid where changes in the polarization of a broad wavelength range of light in a light path in which said light has passed in an incident light beam from a light source to said solid, and after reflection from a point on the surface of said solid, in a reflected light beam to a detector of said changes in polarization, said changes being correlated with features of said solid, the improvement for the measurement of thicknesses of less than 10 nanometers comprising in combination:

said apparatus having a specular arrangement wherein the angle of incidence of said incident light beam and the angle of reflection of said reflected light beam are in a plane and said angle of incidence and said angle of reflection are equal, said light in said light path having a continuum photon energy range of from about 2.75 to about 9.0 eV, said light being in a controlled ambient from a source of said light to a detector of said polarization changes in said light after said reflection.

2. The metrology apparatus improvement for less than 10 nanometer measurement of claim 1 including, in analysis of said polarization changes, in said detector, the reliability of inferred sample parameters, that are derived from said polarization changes, is tested.

3. The metrology apparatus improvement for less than 10 nanometer measurement of claim 2 including in said testing, a comparison that establishes whether a fitting algorithm is indicating a global minimum, said comparison being based on, relation of "goodness of fit" value data with data obtained for "good" and "bad" fits to tabulated simulated data, to which known quantities of noise have been added.

4. The metrology apparatus improvement for less than 10 nanometer measurement of claim 2 including in said comparison iterative convergence testing of widely divergent models.

5. Apparatus for measurement of thicknesses of the order of less than 10 nanometers in a sample of a solid material, comprising:

a specular ellipsometric measurement device wherein changes in the polarization of a broad wavelength range of light with a precise continuum intensity range of about 2.75 to about 9.0 eV occur in a controlled environment light path in which said light has passed in an incident light beam from a light source to a point on said sample and after reflection from said point on said sample, in a reflected light beam to a detector of said changes in polarization, and wherein signals of said changes in polarization are correlated with features of said solid, by comparing inferred parameters of features of said solid indicated by said polarization changes with calculated parameters iteratively until the data indicates reliability of the inferred parameters.

6. The apparatus of claim 5 wherein said signals of said changes in polarization include taking closely spaced data points over the entire said broad wavelength range, comparing previously tabulated results based on parameters similar to said inferred parameters and iteratively modifying both said inferred parameters and said previously tabulated parameters to minimize any disagreement, using simulations with added noise in determination of attainable quality of inferred parameters based on said minimized disagreement parameter values.

7. In measurements of the order of less than 10 nanometers of a solid material where changes in the polarization of a broad wavelength range of light in a light path in which said light has passed in an incident light beam from a light source to said solid material, and after reflection from a point on the surface of said solid material, in a reflected light beam to a detector of said changes in polarization, said changes being correlated with measurements of said solid material, the improvement comprising in combination:

said apparatus having a specular arrangement wherein the angle of incidence of said incident light beam and the angle of reflection of said reflected light beam are in a plane and said angle of incidence and said angle of reflection are equal, said light in said light path having a continuum photon energy range of from about 2.75 to about 9.0 eV, said light being in a controlled ambient from a source of said light to a detector of said polarization changes in said light after said reflection, and, wherein, in analysis of aid polarization changes, the reliability of inferred sample parameters that are derived from said polarization changes, is established by a comparison that established whether a fitting algorithm in indicating a global minimum, said comparison being based on relation of "goodness of fit" value data with data obtained for "good" and "bad" fits, to tabulated simulated data to which known quantities of noise have been added.

8. The method of improving the sensitivity and signal distinguishing ability of reflected light characterization of solids, for sub 10 nanometer thickness measurement comprising in combination the steps of:

providing in a specular broad wavelength light path that includes a serial assembly of; a 2.75–9.0 eV photon energy light source component, an incident light beam, an initial polarizer component, reflection from the surface of a sample of a solid under study, a reflected light beam and a sensing capability for polarization changes in said reflected light beam that are imparted into said reflected light beam in said reflection from said surface, enclosing all of said light path in a signal absorption and signal definiteness limiting controlled ambient, and, performing analytical operations in refining an initial assumption of parameters of said sample by taking closely spaced data points over the entire said wavelength range, comparing previously tabulated results based on parameters of said sample that are similar to said initial assumption parameters, and, iteratively modifying both said sample parameters and said parameters from said tabulated parameters to minimize any disagreement using simulations with added noise in determination of attainable quality of inferred parameters based on said minimized disagreement parameter values.

* * * * *